United States Patent
Wade et al.

(10) Patent No.: US 11,268,928 B2
(45) Date of Patent: Mar. 8, 2022

(54) COMPACT GAS SENSOR INCLUDING A MEMS ELEMENT HAVING CAPILLARIES TO FACILITATE GAS DIFFUSION

(71) Applicant: Honeywell International Inc., Morris Plains, NJ (US)

(72) Inventors: Richard Wade, Worthington, OH (US); Keith Francis Edwin Pratt, Portsmouth (GB); Robert Higashi, Shorewood, MN (US); Scott Edward Beck, Murphy, TX (US); Vijayakumar S, Bangalore (IN); Cristian Diaconu, Bucharest (RO)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 227 days.

(21) Appl. No.: 16/019,373

(22) Filed: Jun. 26, 2018

(65) Prior Publication Data
US 2018/0372675 A1     Dec. 27, 2018

Related U.S. Application Data

(60) Provisional application No. 62/525,700, filed on Jun. 27, 2017.

(51) Int. Cl.
*G01N 27/407*    (2006.01)
*G01N 33/00*     (2006.01)
(Continued)

(52) U.S. Cl.
CPC ......... *G01N 27/4074* (2013.01); *B81B 1/004* (2013.01); *G01N 27/4045* (2013.01);
(Continued)

(58) Field of Classification Search
CPC ........... G01N 27/4074; G01N 27/4045; G01N 27/4076; G01N 33/004; G01N 27/304;
(Continued)

(56) References Cited

U.S. PATENT DOCUMENTS 5,547,554 A * 8/1996 Kiesele .............. G01N 27/4045
                                                    204/415
5,547,555 A * 8/1996 Schwartz ........... G01N 27/3275
                                                    204/403.03

(Continued)

OTHER PUBLICATIONS

Gatty et al. (HK Gatty, G Stemme, N Roxhed, A wafer-level liquid cavity integrated amperometric gas sensor with ppb-level nitric oxide gas sensitivity, J. Micromech. Microeng., 25 (2015) 105013) (Year: 2015).*

*Primary Examiner* — Joshua L Allen
(74) *Attorney, Agent, or Firm* — Alston & Bird LLP

(57) ABSTRACT

Apparatus and associated methods relate to a compact gas sensor (CGS) including a housing with a central stepped cavity with one or more first lead contact(s) forming a portion of a base plane in a bottom of the cavity and one or more second lead contact(s) forming a portion of a stepped plane higher than the base plane, the cavity sized to receive a chemically based stack of material made up of a bottom diffusion electrode layer, a middle electrolyte gel layer, and a top diffusion electrode layer. The bottom diffusion electrode layer is in electrical contact with the first lead contact(s). The top diffusion electrode layer electrically couples to the second lead contact(s) via an overlaying micro electromechanical system (MEMS) element layer with conductive coating. In an illustrative example, the CGS may provide gas sensing in small spaces.

19 Claims, 16 Drawing Sheets

(51) Int. Cl.
  *B81B 1/00* (2006.01)
  *G01N 27/404* (2006.01)
  *G01N 27/406* (2006.01)
  *G01N 27/30* (2006.01)

(52) U.S. Cl.
  CPC ....... *G01N 27/4076* (2013.01); *G01N 33/004* (2013.01); *B81B 2201/0214* (2013.01); *G01N 27/304* (2013.01); *G01N 27/4062* (2013.01)

(58) Field of Classification Search
  CPC ....... G01N 27/4062; G01N 27/406–41; G01N 33/0004–0075; B81B 1/004; B81B 2201/0214
  See application file for complete search history.

(56) References Cited

U.S. PATENT DOCUMENTS

| | | | |
|---|---|---|---|
| 5,830,337 A * | 11/1998 | Xu | G01N 27/4045 204/400 |
| 2002/0121438 A1 * | 9/2002 | Saffell | G01N 27/4045 204/415 |
| 2003/0209442 A1 * | 11/2003 | Harper | G01N 33/004 205/108 |
| 2004/0026246 A1 | 2/2004 | Chapples et al. | |
| 2005/0145493 A1 * | 7/2005 | Saffell | G01N 27/4045 204/431 |
| 2010/0200664 A1 * | 8/2010 | Drew | G01N 33/004 236/94 |
| 2013/0062223 A1 * | 3/2013 | Rabbett | G01N 27/4074 205/793 |
| 2014/0105790 A1 * | 4/2014 | Gaudon | G01N 27/16 422/90 |
| 2014/0311905 A1 * | 10/2014 | Stetter | B01J 31/06 204/424 |
| 2015/0001076 A1 * | 1/2015 | Porro | G01N 33/0027 204/412 |
| 2015/0123073 A1 * | 5/2015 | Lei | B82Y 15/00 257/12 |
| 2016/0178565 A1 * | 6/2016 | Chapples | G01N 27/407 204/412 |

* cited by examiner

Solid Polymer Electrolyte Constituents

| Chemical | CAS No | Supplier | Grade | Cat No |
|---|---|---|---|---|
| Poly(vinylidene fluoride-co-hexafluoropropylene) | - | Solvay | Solef 21216 | - |
| Bistrifluoromethanesulfonimide | 82113-65-3 | Fluka | Purum (97%) | 15220 |
| Butyl Sulfone | 598-04-9 | Aldrich | 99% | B10,220-2 |
| Acetone (RM4) | 67-64-1 | BDH | AnalaR | 100034Q |
| 2-Pentanone | 107-87-9 | Aldrich | >99% | 53,774-8 |
| Methyl Sulfoxide | 67-68-5 | Fluka | Purum (>99%) | 41650 |

FIG. 9B

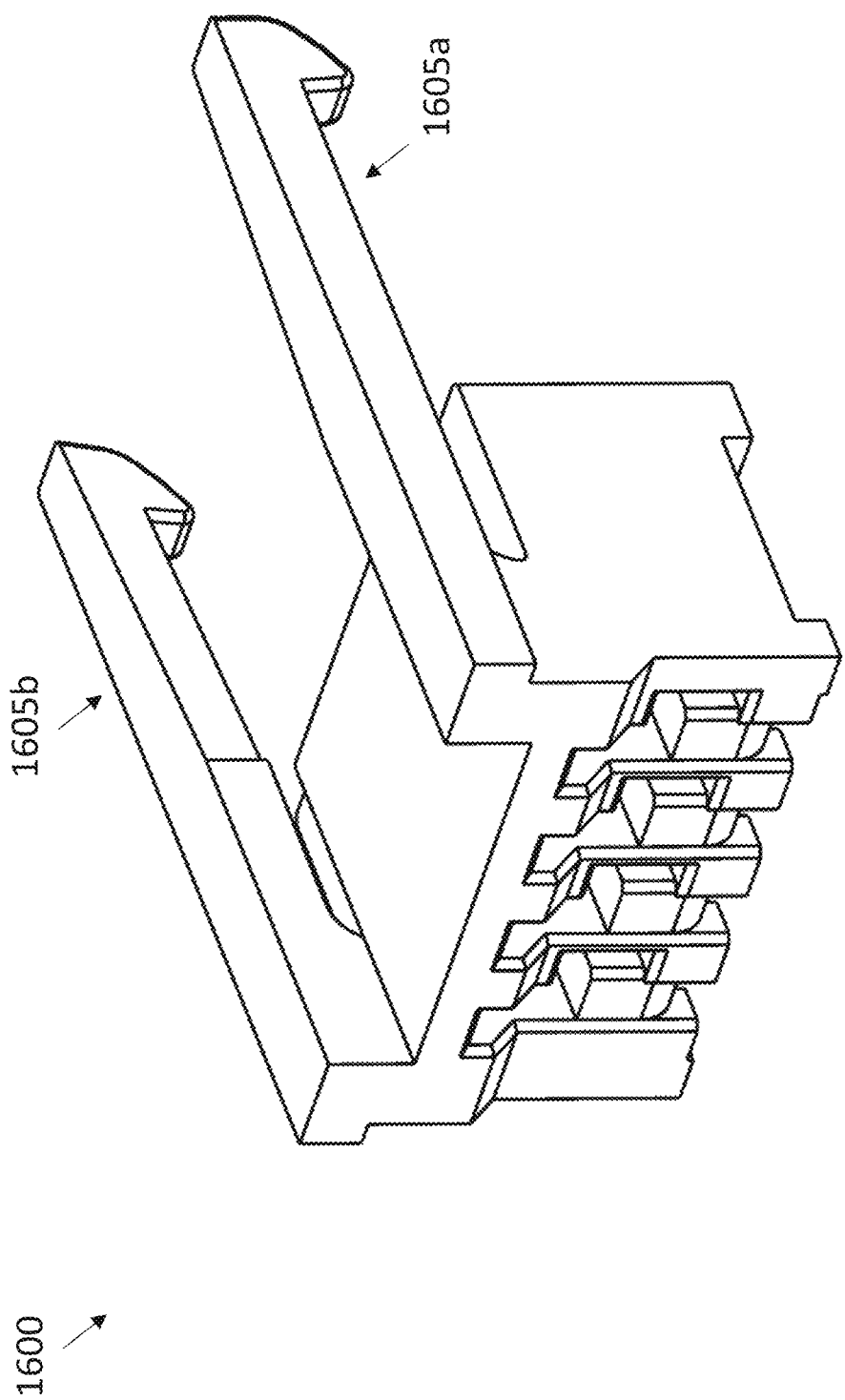

COMPACT GAS SENSOR INCLUDING A MEMS ELEMENT HAVING CAPILLARIES TO FACILITATE GAS DIFFUSION

CROSS-REFERENCE TO RELATED APPLICATIONS

This application claims the benefit of U.S. Provisional Application Ser. No. 62/525,700 titled "Compact Gas Sensor," filed by Wade, et al. on Jun. 27, 2017.

This application incorporates the entire contents of the foregoing application(s) herein by reference.

TECHNICAL FIELD

Various embodiments relate generally to gas sensors.

BACKGROUND

Electrochemical gas sensors are gas detectors that measure the concentration of a target gas by oxidizing or reducing the target gas at an electrode and measuring the resulting current. These types of sensors may contain several electrodes in contact with an electrolyte. Gas may diffuse into the sensor, through the back of the porous membrane to the working electrode where it is oxidized or reduced. This electrochemical reaction results in an electric current that may pass through an external circuit.

Gas sensors may be employed for personal safety in settings where dangerous gases may suddenly exist. The sensors may trigger audible alarms and/or visible warning lights. As sensing technology progresses, gas sensors may be found in increasing numbers of new applications.

SUMMARY

Apparatus and associated methods relate to a compact gas sensor (CGS) including a housing with a central stepped cavity with one or more first lead contact(s) forming a portion of a base plane in a bottom of the cavity and one or more second lead contact(s) forming a portion of a stepped plane higher than the base plane, the cavity sized to receive a chemically based stack of material made up of a bottom diffusion electrode layer, a middle electrolyte gel layer, and a top diffusion electrode layer. The bottom diffusion electrode layer is in electrical contact with the first lead contact(s). The top diffusion electrode layer electrically couples to the second lead contact(s) via an overlaying micro electromechanical system (MEMS) element layer with conductive coating. In an illustrative example, the CGS may provide gas sensing in small spaces.

The MEMS element further includes an array of apertures, placed to pass gases from ambient air to the top diffusion layer. Gases passing through the MEMS element contact the top diffusion layer. The incident gases in conjunction with the electrodes, electrolyte gel and the top diffusion layer, cause a chemical reaction. The reaction causes a transfer of electrons, which results in an electric current through the electrodes and contacts, a counter-reaction occurs on the bottom electrode to complete the circuit. The contacts form external pins that exit the housing. Designers may connect the pins to application specific electronics. The CGS is further configured for surface-mount board assembly and reflow temperatures by employment of a sensor receptacle, the receptacle employing high temperature material to allow reflow operations, and to allow connection to the CGS after board assembly.

Various embodiments may achieve one or more advantages. For example, some embodiments may be durable and stable, and may provide extended sensor life. In some examples, the smaller size of the CGS may better fit customer's compact applications.

The details of various embodiments are set forth in the accompanying drawings and the description below. Other features and advantages will be apparent from the description and drawings, and from the claims.

BRIEF DESCRIPTION OF THE DRAWINGS

FIG. 9B depicts exemplary constituents of an exemplary solid polymer electrolyte.

FIG. 16 depicts an exemplary an exemplary CGS board mountable sensor receptacle with supporting latch arms.

Like reference symbols in the various drawings indicate like elements.

DETAILED DESCRIPTION OF ILLUSTRATIVE EMBODIMENTS

Figure 1:
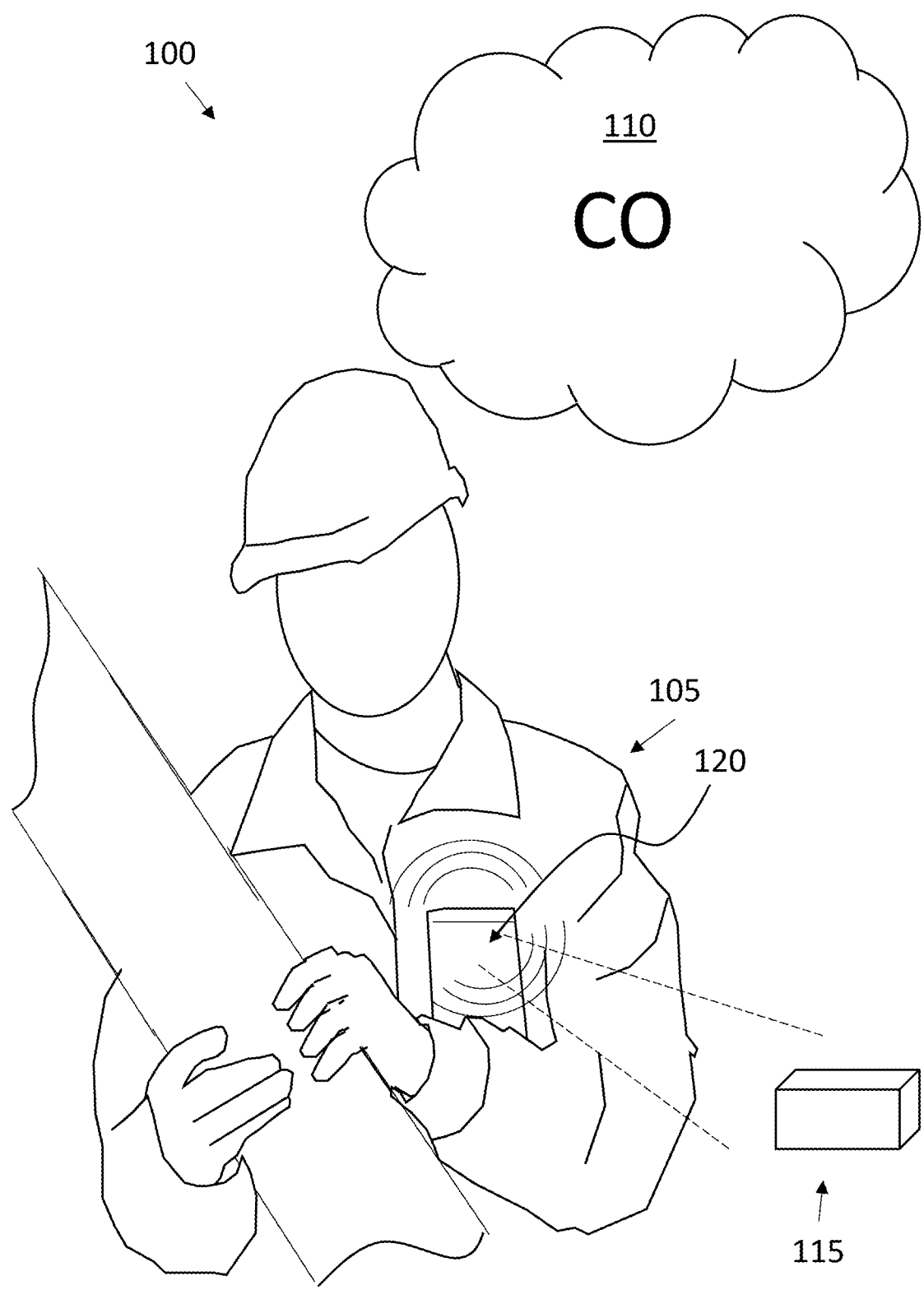
FIG. 1 depicts a perspective view of a use case scenario of an exemplary compact gas sensor (CGS).

FIG. 1 depicts a perspective view of a use case scenario of an exemplary compact gas sensor (CGS). A use case scenario 100 shows a person 105 in the proximity of a carbon monoxide gas 110. Because carbon monoxide is an odorless gas, the person 105 may not detect that there is a toxic level of the carbon monoxide gas 110 in his or her vicinity. Because of its small size, the person 105 is able to comfortably wear a CGS assembly 115, which detects the presence of the carbon monoxide gas 110. The CGS assembly 115 is attached at a point on the user's clothes 120.

Figure 2:
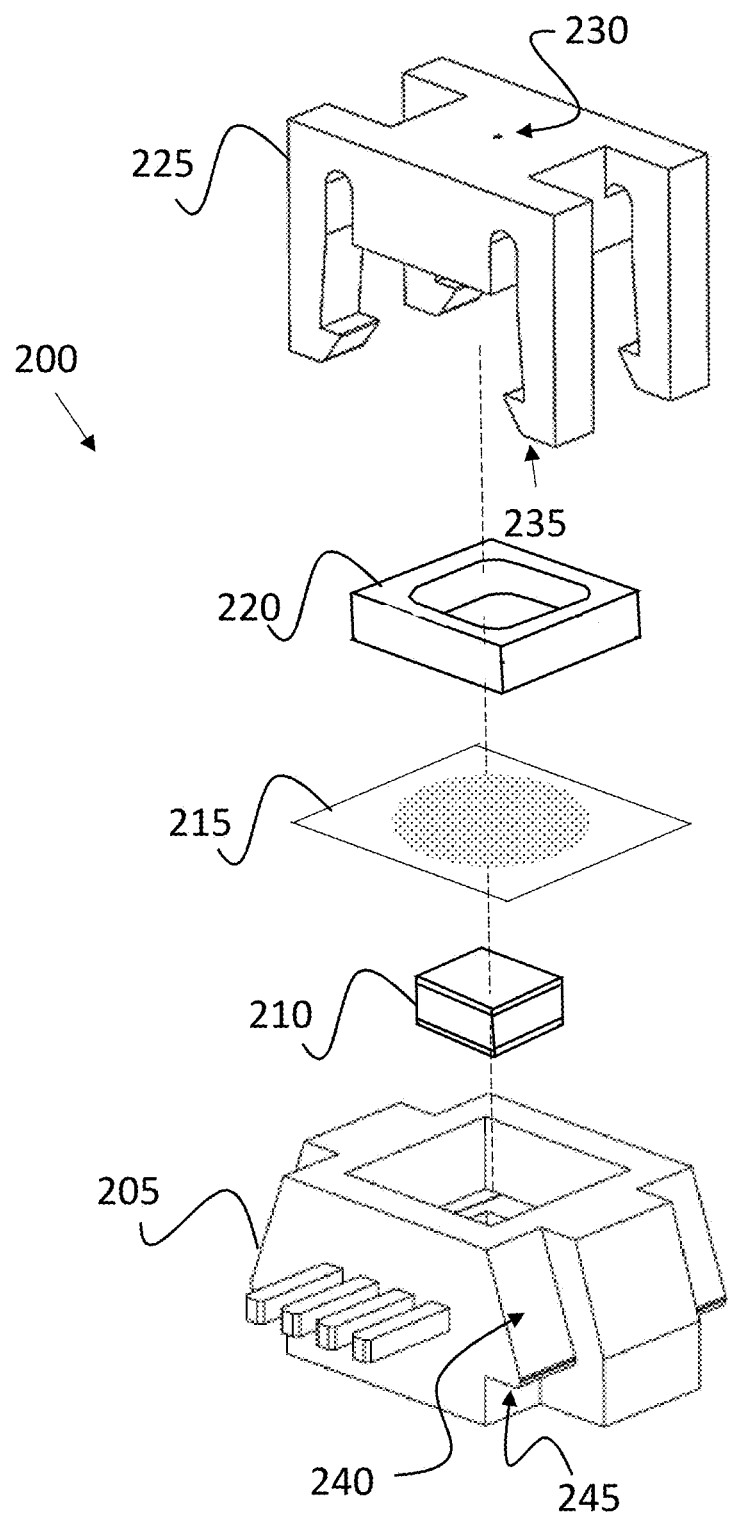
FIG. 2 depicts a perspective exploded view of an exemplary CGS.

FIG. 2 depicts a perspective exploded view of an exemplary CGS. A CGS 200 includes a sensor housing 205. The sensor housing 205 receives a gel electrolyte subassembly 210. The gel electrolyte subassembly 210 is electrically connected to the sensor housing 205 by a platinum-plated MEMS element 215. The platinum-plated MEMS element 215 is surmounted by a compliant media seal 220. The platinum-plated MEMS element 215 is forcibly held in place by the compliant media seal 220 and by a lid 225, which over-clamps the underlying components. The lid 225 includes a gas inlet aperture 230. In an illustrative example, sample gases may enter the CGS 200 through the gas inlet aperture 230. The gas may continue through the compliant media seal 220 and through the platinum-plated MEMS element 215. Finally, the gas makes its way to the gel electrolyte subassembly 210, where a chemical reaction occurs. See FIG. 10 for further details.

The lid 225 includes a latching finger 235. The latching finger travels down a housing slope face 240, deflecting the latching finger 235 slightly. Once fully engaged, the latching finger 235 snaps into place under a housing latch ledge 245. In some embodiments, the design of the lid 225 may be operable to compress the compliant media seal 220.

Figure 3:
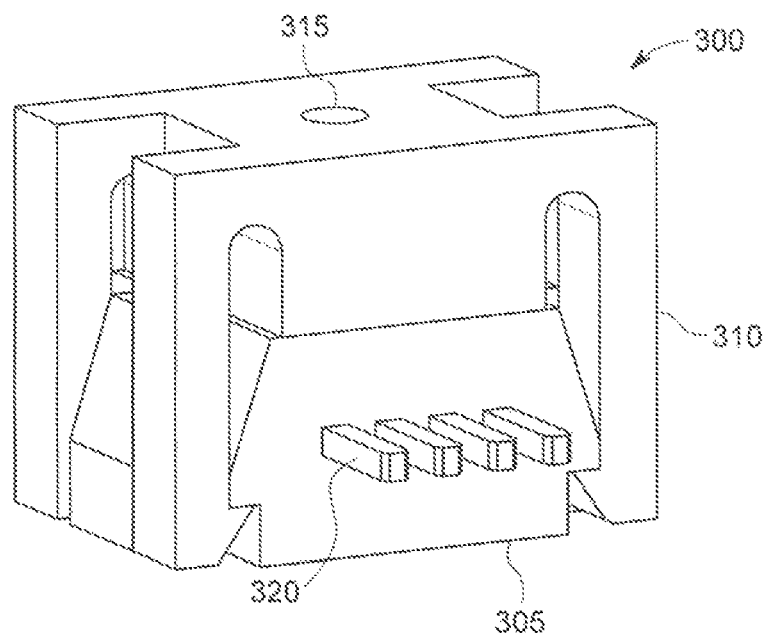
FIG. 3 depicts a perspective view of an exemplary CGS in an assembled state.

FIG. 3 depicts a perspective of an exemplary CGS in an assembled state. A CGS 300 includes a base housing 305. The base housing 305 is latchably engaged with an over-clamp lid 310. The over clamp lid 310 includes a gas inlet aperture 315. The base housing 305 is moldably engaged with a contact 320. In some embodiments, the contacts 320 may be a unitary shape exiting within a cavity (reference FIG. 10, items 1005 and 1010) within the base housing 305. In some examples, product concept dimensions may be for reference without terminal length. Size may vary based on the final connector selection. The material used for the base housing 305 and the lid 310 may be plastic. Plastic employed may withstand the holding force for medial seal and electrolyte compression.

Figure 4:
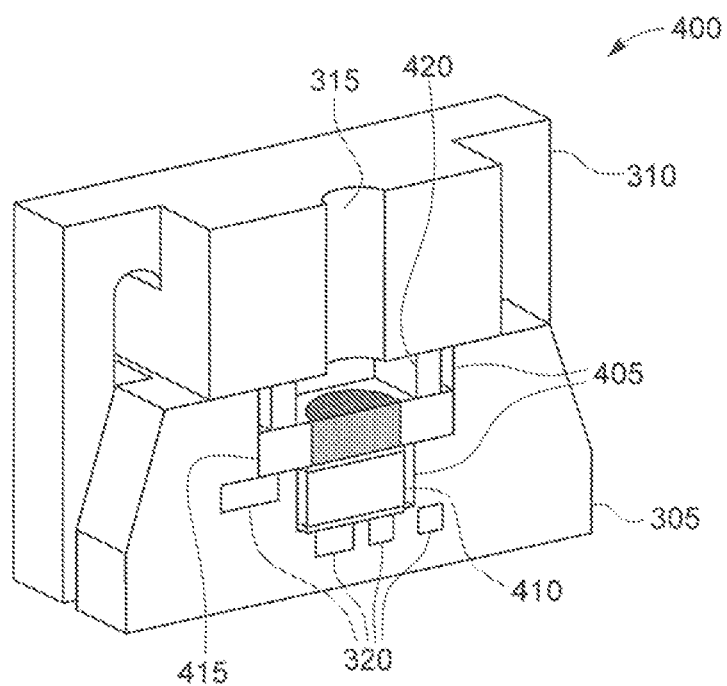
FIG. 4 depicts a perspective cross-sectional view of an exemplary CGS in an assembled state.

FIG. 4 depicts a perspective cross-sectional view of an exemplary CGS in an assembled state. A CGS 400 as depicted in FIG. 3 item 300, is shown with a cross-sectional view to show inner components and relative locations. The CGS 400 includes the base housing 305. The base housing 305 is latchably engaged with the over-clamp lid 310. The over clamp lid 310 includes the gas inlet aperture 315. The base housing 305 is moldably engaged with the contact 320. In some embodiments, the contacts 320 may be a unitary shape exiting within a cavity 405 within the base housing 305. Refer to FIG. 10 for additional views of the cavity 405. Within the cavity 405 is a sensing element 410. The sensing element 410 is proximate a MEMS silicon element 415. In various examples, the MEMS silicon element 415 may be laser drilled. In some examples, the MEMS silicon element 415 may be etched with an array of apertures by employment of "deep reactive ion etching." In some examples, the array of apertures may allow the gas to feed the MEMS silicon element 415. The MEMS silicon element 415 may be coated with platinum. The platinum may be employed to electrically couple to the one or more contacts 320. To hold the sensing element 410 in compression with the above proximate MEMS silicon element 415 and with the contacts 320 at the base of the cavity 405, a compliant media seal 420 (e.g., Vitron rubber, fluorosilicone rubber) is added to the component stack. Above of the compliant media seal 420 is located the over clamp lid 310. In some embodiments, the over clamp lid 310 is snapped into the housing 305, compressing the media seal 420 against the silicon element 415 to force the component stack into electrical conduction.

In some embodiments, the over clamp lid 310 may also facilitate a diffusion limited process. The process may be controlled by limiting the diffusion of the sense gas into the CGS 400 with a restriction. The restriction may be created by placing a small aperture 315 (e.g., 15 µm diameter) through the material of the lid 310 for a length (e.g., 1500 µm). This ratio of diameter/length 1:100 may create the restriction. In some examples, the aperture 315 may be about 10 µm, 20 µm, 30 µm, 40 µm, 50 µm, 60 µm, 70 µm, 80 µm, 90 µm, or about 100 µm in diameter. In some embodiments, the aperture 315 may be about 100 µm, 200 µm, 300 µm, 400 µm, 500 µm, 600 µm, 700 µm, 800 µm, 900 µm, or about 1000 µm in diameter.

Figure 5:
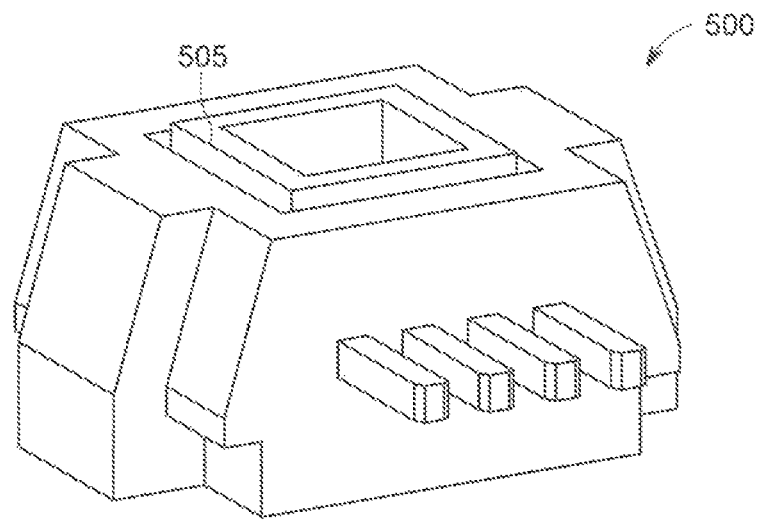
FIG. 5 depicts a perspective view of an exemplary CGS illustrating a compliant media seal.

FIG. 5 depicts a perspective view of an exemplary CGS illustrating a compliant media seal. A CGS 500 includes a compliant media seal 505.

Figure 6:
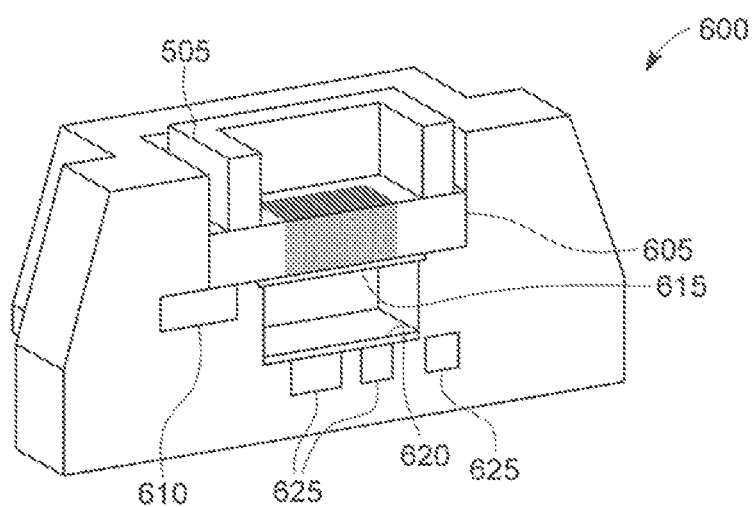
FIG. 6 depicts a perspective cross-sectional view of an exemplary CGS illustrating a compliant media seal.

FIG. 6 depicts a perspective cross-sectional view of an exemplary CGS illustrating a compliant media seal. A CGS in cross section 600 includes the compliant media seal 505. The compliant media seal 505 rests upon a MEMS element 605. The MEMS element 605 is in electrical contact with a working electrode 610. The MEMS element 605 is also in electrical contact with a top diffusion electrode layer 615 of the electrolyte. In some embodiments, ions may be generated at the interface between the electrolyte and electrode. This may result in an electrical current moving between the top diffusion electrode layer 615 and a bottom diffusion electrode layer 620. The bottom diffusion electrode layer 620 is in electrical contact with one or more housing contacts 625. It is noteworthy that the gel electrolyte which is present in the CGS, has been hidden in FIG. 6 to facilitate viewing of other structures.

Figure 7A:
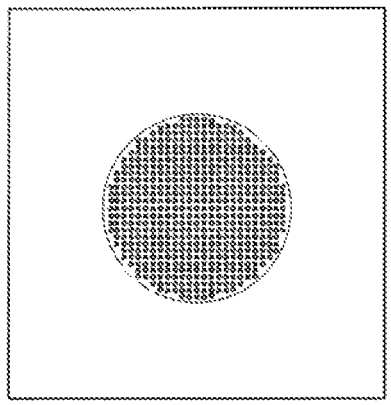
FIGS. 7A, 7B, 7C, and 7D depict plan views of various exemplary MEMS elements.
Figure 7B:
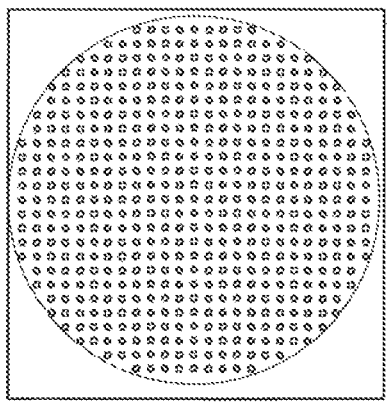
Figure 7C:
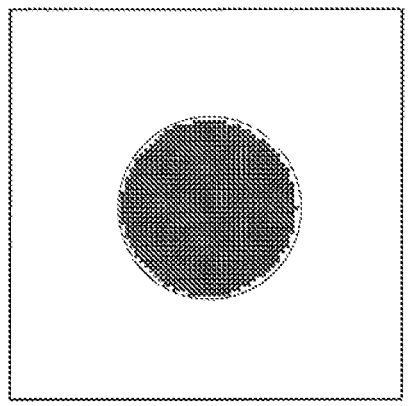
Figure 7D:
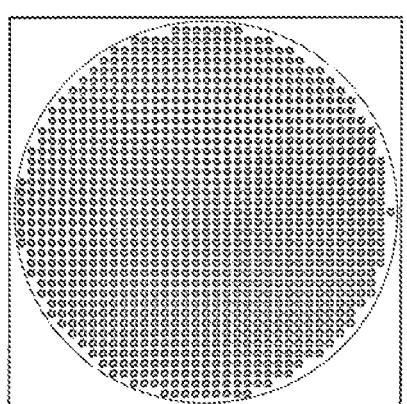
Figure 8A:
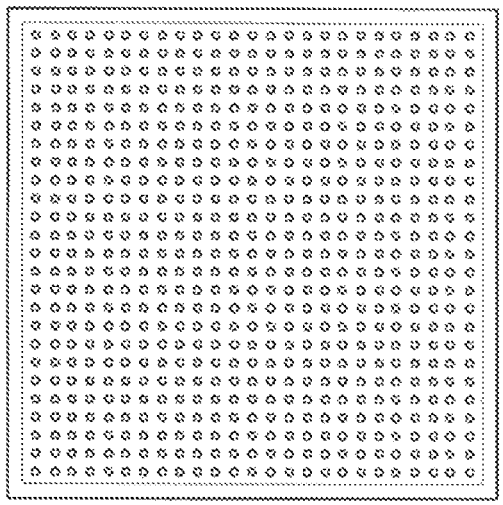
FIGS. 8A, 8B, 8C, and 8D depict plan views of various exemplary MEMS elements.
Figure 8B:
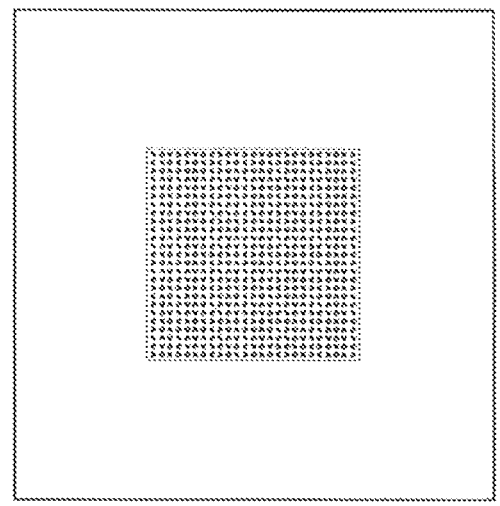
Figure 8C:
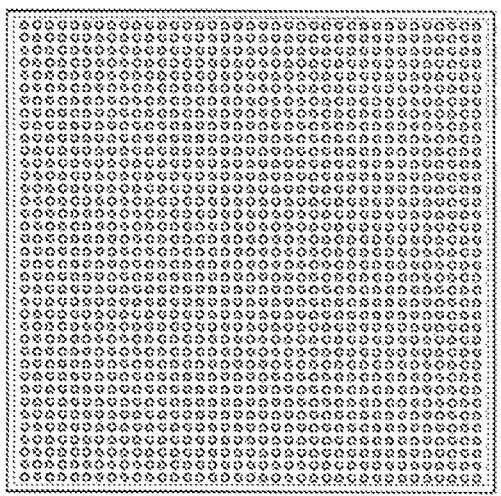
Figure 8D:
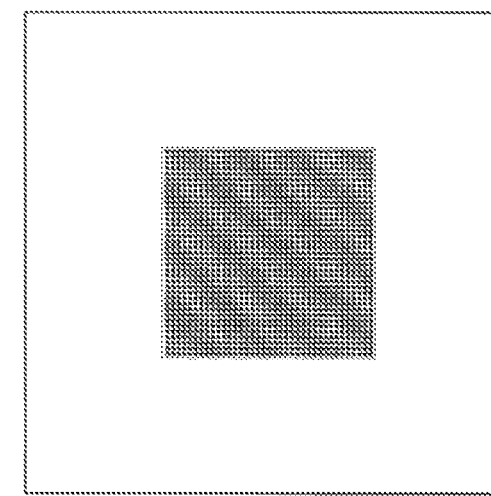

FIGS. 7A, 7B, 7C, and 7D depict a plan views of various exemplary MEMS elements. In FIGS. 7A-7B, maintaining a 0.035 mm distance between holes produces 517 holes with a diameter of 0.9 mm. In FIGS. 7C-7D, maintaining a 0.025 mm distance between holes produces 1009 holes with a diameter of 0.9 mm. The hole spacing, hole diameter, and number of holes may be greater or less than the above parameters. In various examples, the MEMS element may be formed as a substantially planar sheet of material. In some examples the MEMS element may have the shape of a square or a circle.

Due to the extremely small diameter of the apertures within the MEMS elements, a process called deep reactive ion etching (DRIE) may be employed. The DRIE process may allow gas to feed the diffusion electrode layer to force the reaction.

The face of the various MEMS elements may be coated with platinum. The platinum may be used for electrical conduction to the working electrode terminal.

In some embodiments, the MEMS elements may be made of silicon. Silicon may advantageously be readily available, inexpensive and high-quality. Since silicon may be employed for incorporation of electronic functionality, it may be suitable for a wide variety of MEMS applications.

FIGS. 8A, 8B, 8C, and 8D depict a plan views of various exemplary MEMS elements. As described in FIGS. 7A-7D, extremely small apertures may be etched into the MEMS elements. The array of apertures may be in a circular pattern as shown in FIGS. 7A-7D. Contrastingly, the array of apertures may be in a square pattern as shown in FIGS. 8A-8D. Other patterns or shapes of apertures may be advantageous, and may be implemented within the MEMS element.

Figure 9A:
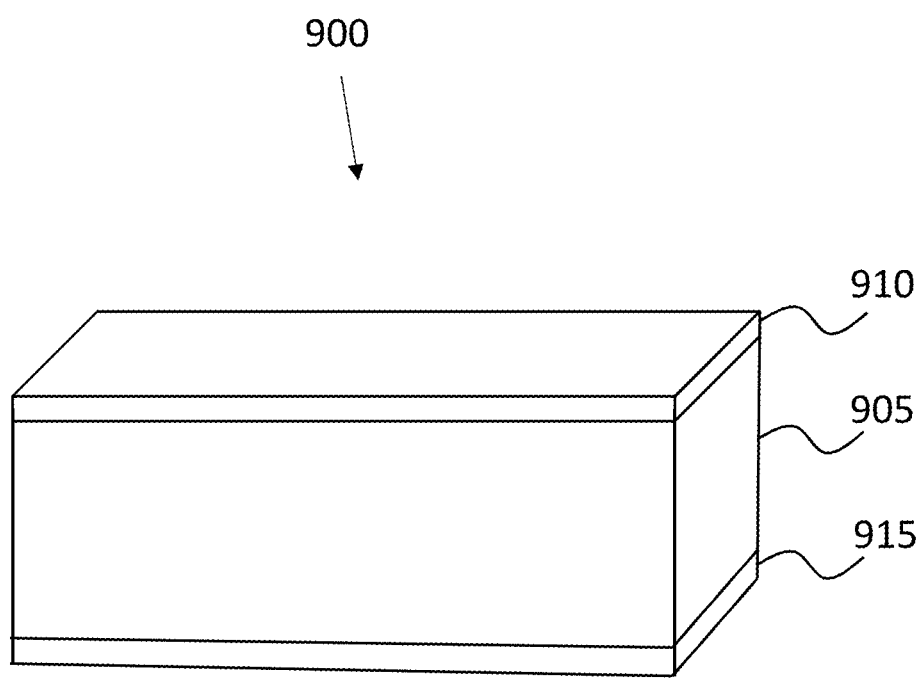
FIG. 9A depicts a perspective view of an exemplary electrolyte stack.

FIG. 9A depicts a perspective view of an exemplary electrolyte stack. An electrolyte stack 900 includes a gel electrolyte 905. The gel electrolyte 905 is sandwiched between two diffusion electrode layers; a top diffusion electrode layer 910 and a bottom diffusion electrode layer 915. In some examples, the electrolyte stack 900 may be sized to fit within a housing cavity pocket 1.2 mm square. In some examples, the electrolyte stack 900 may be sized to fit in a housing cavity pocket of 1 mm square. The electrolyte stack 900 may be sized to fit within a housing cavity pocket having a volume greater or less than these numbers. Furthermore, the housing cavity pocket may have a non-square shape. In some embodiments, the electrolyte gel may greatly extend the life of the chemical sensor. In some examples, the electrolyte gel may be substantially durable and stable.

FIG. 9B depicts exemplary constituents of an exemplary solid polymer electrolyte.

Figure 10A:
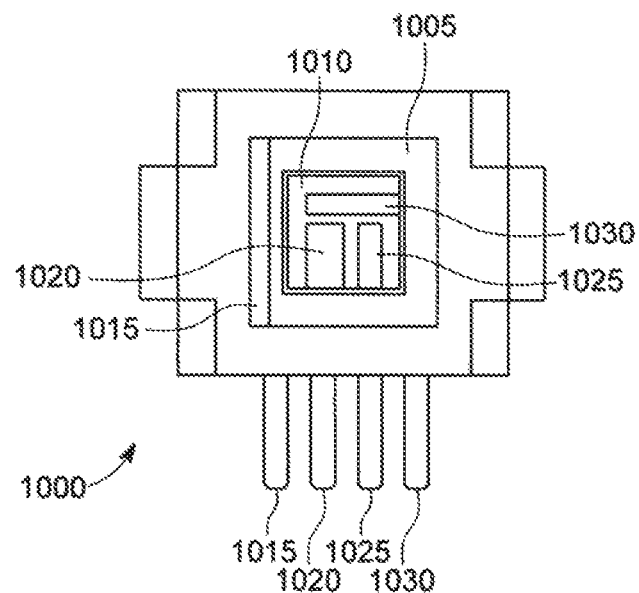
FIG. 10A depicts a top view of an exemplary CGS housing.
Figure 10B:
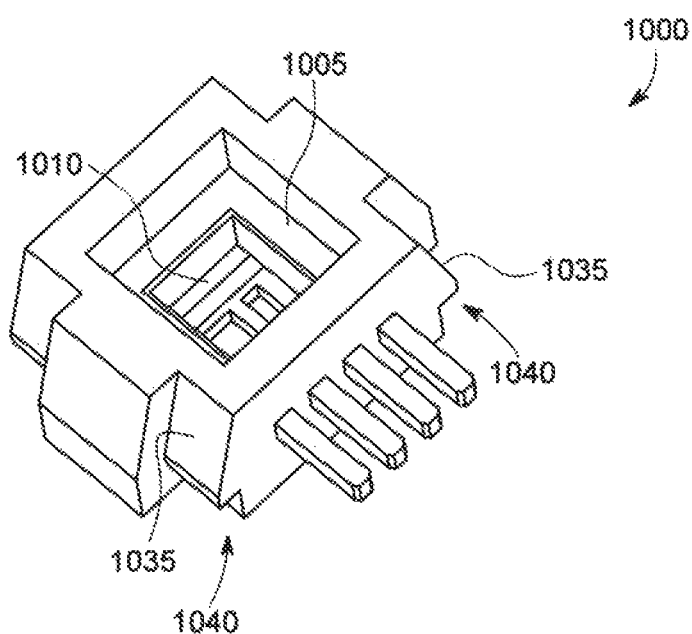
FIG. 10B depicts a perspective view of an exemplary CGS housing.

FIG. 10A depicts a top view of an exemplary CGS housing. FIG. 10B depicts a perspective view of an exemplary CGS housing. A CGS housing 1000 includes a central cavity made up of a cavity upper deck 1005 and a cavity lower deck 1010. The cavity upper deck 1005 is moldably engaged with a working electrode contact 1015. The cavity lower deck 1010 is moldably engaged with a counter electrode contact 1020, a diagnostic electrode contact 1025, and a reference electrode contact 1030. Each of the described electrode contacts 1015, 1020, 1025, and 1030 are elongated unitary conductors exiting the CGS perpendicular to a CGS external horizontal wall. The electrode contacts 1015, 1020, 1025 and 1030, though not all on the same plane within the cavity decks 1005 and 1010, exit the CGS in a central horizontal plane, and parallel with one another. In some embodiments, rather than acting as contacts to the gas diffusion electrode layer(s), the electrode contacts 1020, 1025 and 1030 may function as electrodes when plated with a suitable material, such as platinum. The CGS 1000 also includes a latching ramp 1035 integrated into the CGS housing 1000 material. At the bottom of the latching ramp 1035 is a latching lip 1040. In an illustrative example, a latching lid (ex: FIG. 2, item 225) attaches to the CGS housing 1000 by pressing the latching lid normal to the cavity bottom. In such examples, each latching finger (ex: FIG. 2, item 235) is forced outward from the center of the CGS housing 1000 until it reaches the latching lip 1040. At this point, the latching finger snaps inward toward the center of the CGS housing 1000, locking the latching lid in a latched relationship with the CGS housing 1000.

In various examples, a chemical reaction may occur at the interface between the electrolyte (FIG. 9A, item 905) and the top diffusion electrode layer (FIG. 9A, item 910) in response to an incident sample gas on the top diffusion electrode layer (FIG. 9A, item 910). This reaction may produce free electrons which may cause electrical current flow through the working electrode contact 1015, and may return to the sensor at the counter electrode contact 1020. In an operational example, the current may flow through an external current measuring circuit such as a resistor or an active current to voltage convertor.

Figure 11A:
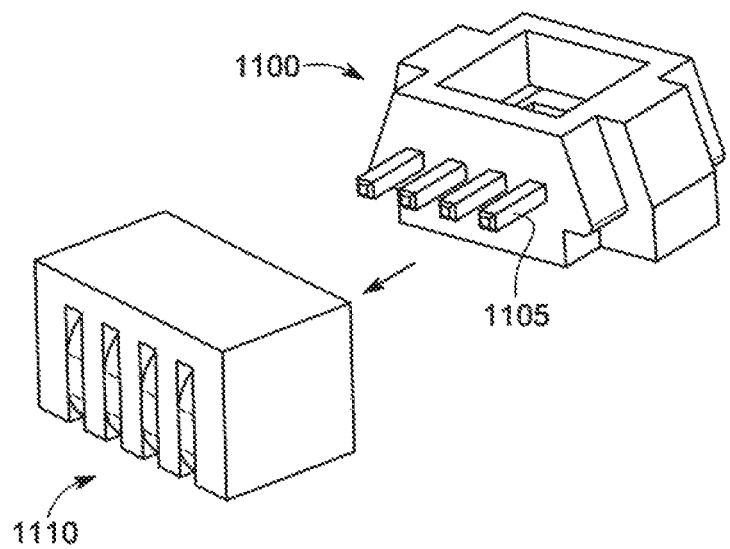
FIGS. 11A, 11B, and 11C depict perspective views of an exemplary CGS board connection scheme.
Figure 11B:
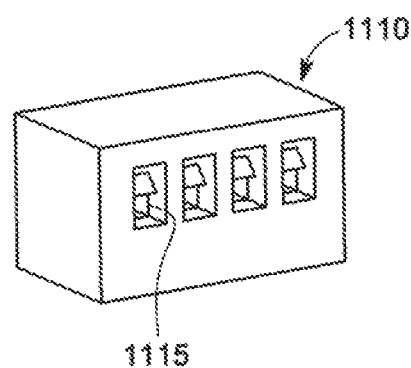
Figure 11C:
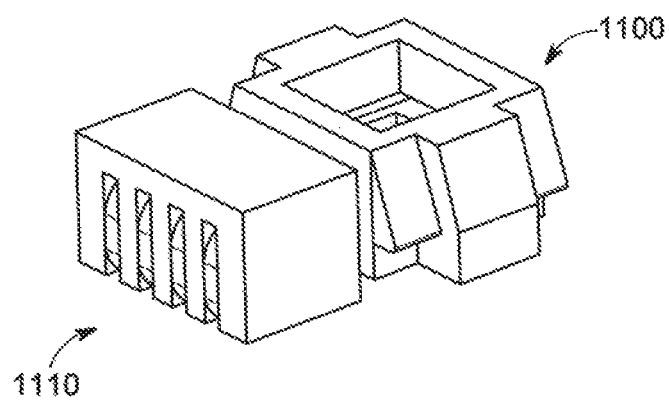

FIGS. 11A, 11B, and 11C depict perspective views of an exemplary CGS board connection scheme. In FIG. 11A, a CGS 1100 includes a sensor pin 1105. The CGS 1100 plugs into a sensor receptacle 1110. As depicted in FIG. 11B, the connection is accomplished when the sensor pin 1105 from FIG. 11A slidably engages and electrically connects to a mating socket 1115 within the sensor receptacle 1110. (The mating socket 1115 is hidden from view on the sensor receptacle 1110 in FIG. 11A.) Next in FIG. 11C, the CGS 1100 is shown in a final mating state to the sensor receptacle 1110.

Figure 12A:
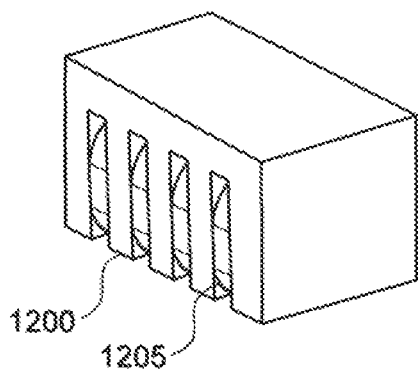
FIGS. 12A, 12B, 12C, and 12D depict various perspective and elevation views of an exemplary CGS board-mountable sensor receptacle.
Figure 12B:
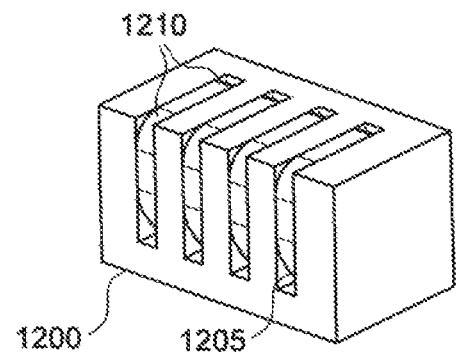
Figure 12C:
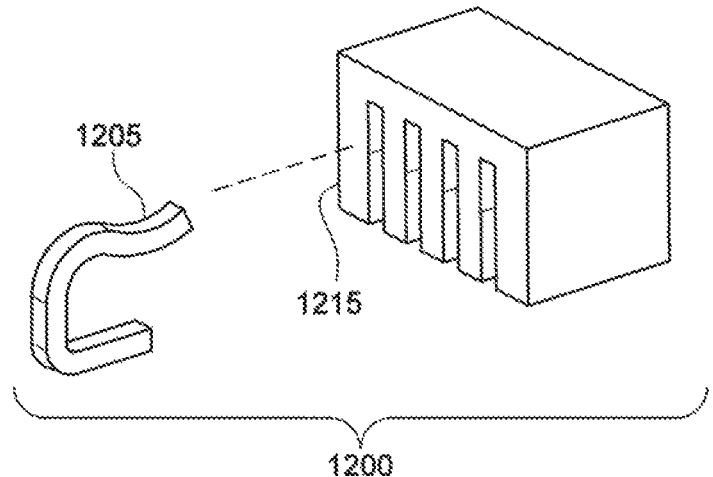
Figure 12D:
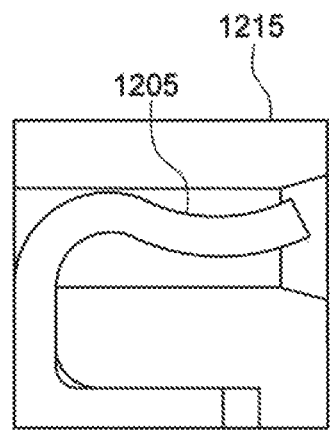

FIGS. 12A, 12B, 12C, and 12D depict various perspective and elevation views of an exemplary CGS board-mountable sensor receptacle. In FIG. 12A, a fully assembled CGS board mountable sensor receptacle 1200 is shown. The sensor receptacle 1200 includes a contact pin 1205. In FIG. 12B the fully assembled CGS board mountable sensor receptacle 1200 is shown upside down to show surface-mount feet 1210, which are part of the contact pin 1205. In FIG. 12C the sensor receptacle 1200 is shown with the contact pin 1205 separated from a receptacle housing 1215. In some embodiments, the contact pins 1205 snap into the sensor receptacle 1200. In FIG. 12D, the contact pin 1205 is shown in detail. A cross-sectional view of the receptacle housing 1215 shows the design detail, illustrating how the contact pin 1205 is positioned in relationship to the receptacle housing 1215.

Figure 13:
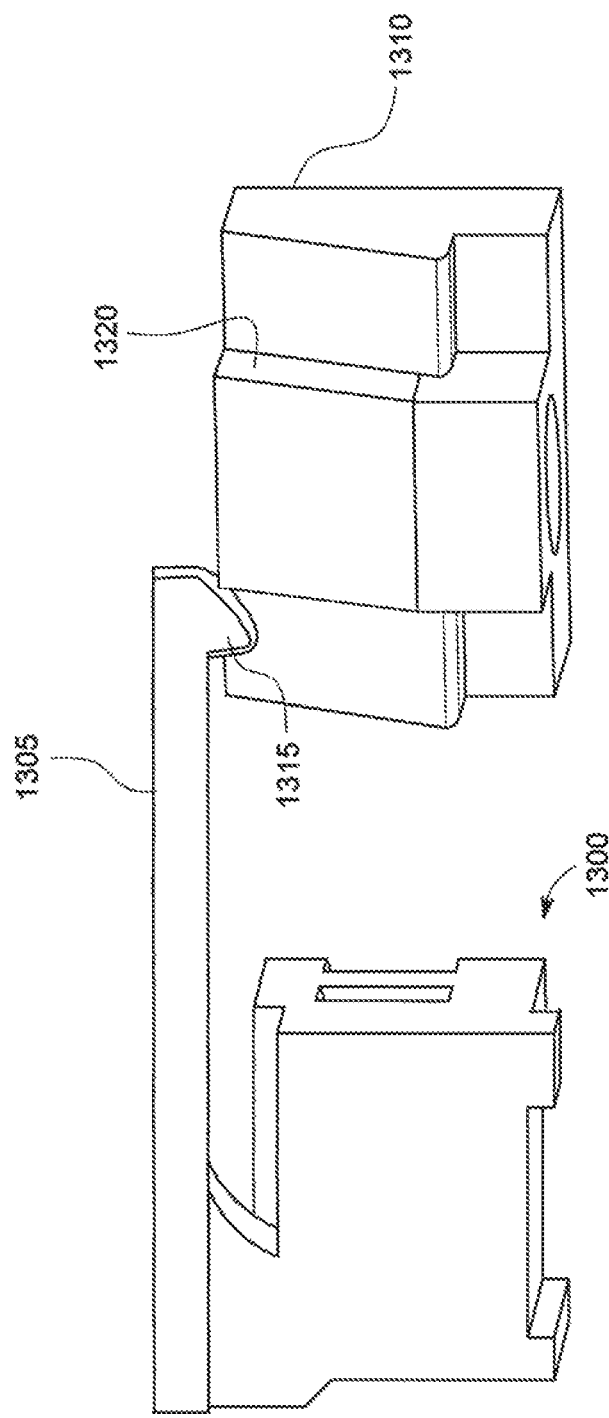
FIG. 13 depicts an exemplary CGS board mountable sensor receptacle with supporting latch arm.

FIG. 13 depicts an exemplary CGS board mountable sensor receptacle with supporting latch arm. A sensor receptacle 1300 includes a support arm 1305. The support arm 1305 is operable to support a sensor 1310 when in electrical engagement with the sensor receptacle 1300. In an illustrative example, without the support arm 1305, anchoring of the sensor 1310 may be provided by the sensor pins (FIG. 3, item 320). Accordingly, the support arm 1305 may provide additional anchoring support to the sensor 1310. Further, the support arm 1305 may latch into place as the sensor 1310 is slid into electrical engagement along the longitudinal axis of the sensor pin contacts (FIG. 3, item 320). When fully engaged, the sensor receptacle 1300 and the sensor 1310 may mate along a sensor receptacle latching surface 1315 and a sensor latching surface 1320. In some examples, the latching operation may be releasable.

Figure 14A:
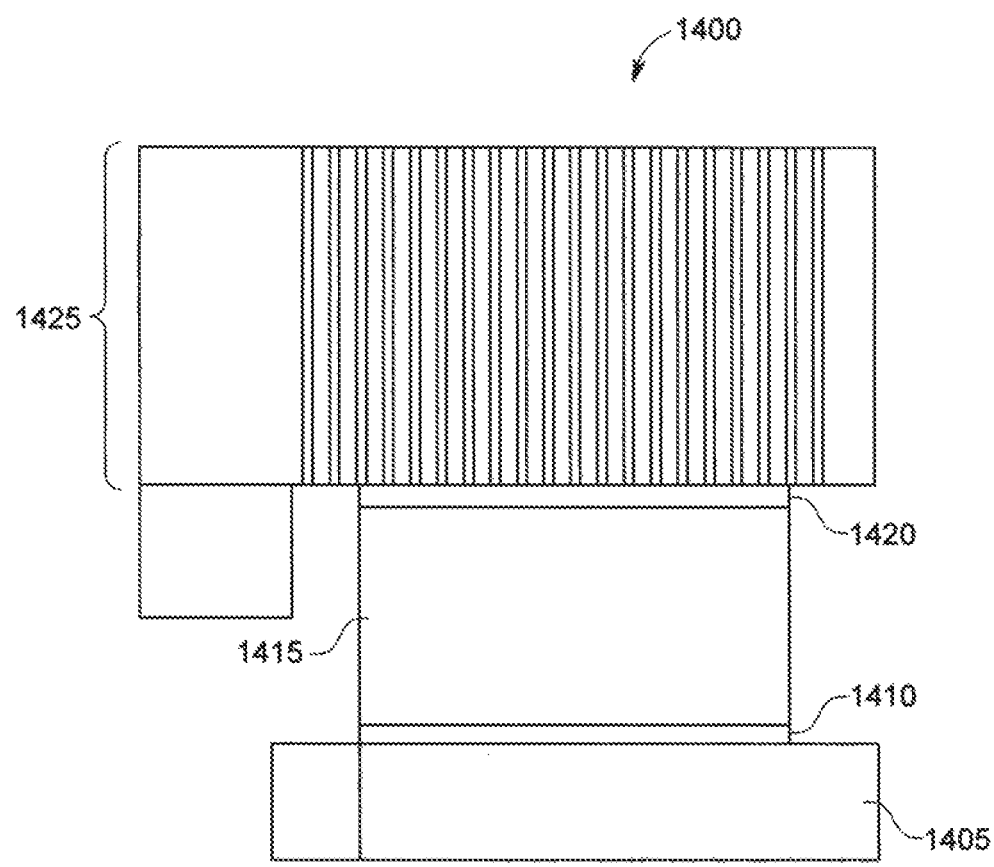
FIG. 14A depicts a cross-sectional view of a CGS stack.

FIG. 14A depicts a cross-sectional view of a CGS stack. A CGS stack 1400 includes a sensor lead 1405. The sensor lead 1405 carries the electron flow out of the CGS sensor (FIG. 3, item 300) via the interface pins (FIG. 3, item 320). The sensor lead 1405 is proximate to, and in electrical contact with, a bottom diffusion electrode layer 1410. The bottom diffusion electrode layer 1410 is fixedly coupled to a gel electrolyte 1415. The gel electrolyte 1415 is fixedly coupled to a top diffusion electrode layer 1420. The top diffusion electrode layer 1420 is proximate to, and in electrical contact with, a MEMS element 1425. In some examples, the MEMS element 1425 may be a silicon diffusion limiting element with platinum plated surfaces. In some examples, the platinum plating may exist only on the bottom surface.

In some embodiments, the gas diffusion electrode layer may not be implemented. In such examples, the plating on the MEMS element may act as the sensing electrode. For example, this configuration may be employed where the target gas is substantially soluble and diffusible in the electrolyte.

In an illustrative example, gases traveling into a CGS sensor housing may become incident to the MEMS element 1425. The gases then make their way through an array of apertures 1430 included within the MEMS element 1425.

Figure 14B:
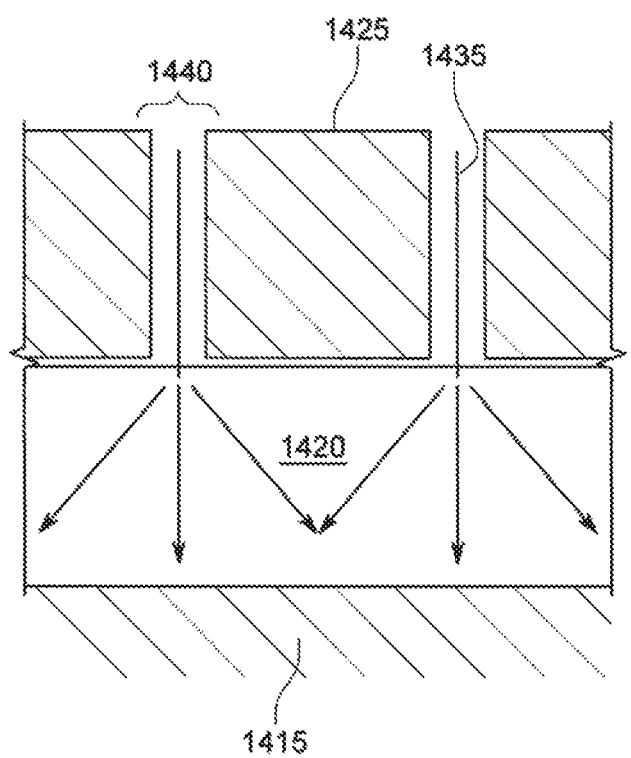
FIG. 14B depicts a cross-sectional view of a gas diffusion principle.

FIG. 14B depicts a cross-sectional view of a gas diffusion principle. Gases 1435 travel from the MEMS element 1425 through each of the capillaries 1440 included in the array of apertures (FIG. 14A, item 1430). Once the gases reach the bottom of the capillary 1440, dispersion of the gases occur within the top dispersion electrode 1420. The top dispersion electrode 1420 is substantially porous and thereby operably employed to spread the gases 1435 over the electrode. The gases 1435 in a dispersed state contact the gel electrolyte 1415. Accordingly, dispersion/spreading of the gases 1435 over the gel electrolyte 1415 may provide efficient use of the gel electrolyte 1415 material.

In some examples, a combination of technologies and principles may be employed to achieve very small holes spaced very close together. Some technologies and principles may employ very thin material that is conductive, and durable enough to be part of a stack of components as depicted in FIG. 14A.

Figure 15:
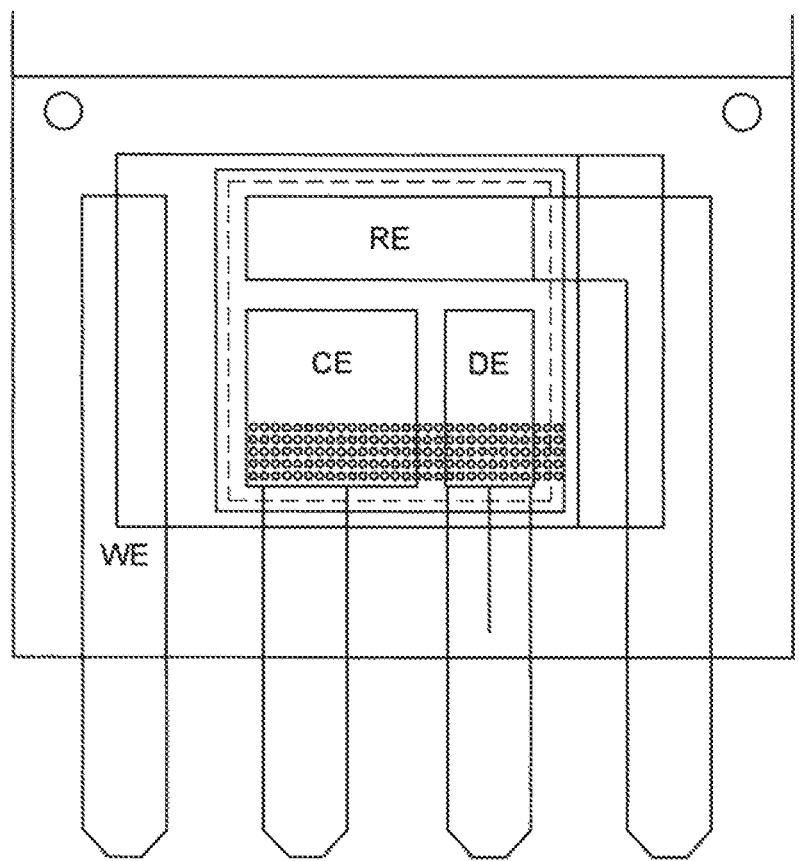
FIG. 15 depicts top view of an exemplary CGS sensor.

FIG. 15 depicts top view of an exemplary CGS sensor. The FIG. 15 embodiments illustrates exemplary terminals, which may be, for example, the working electrode (WE), the control electrode (CE), the diagnostic electrode (DE) and a reference electrode (RE).

FIG. 16 depicts an exemplary CGS board mountable sensor receptacle with supporting latch arms. A sensor receptacle 1600 includes a first support arm 1605a and a second support arm 1605b. The support arms 1605a-b are operable to support a sensor (not shown) when in electrical engagement with the sensor receptacle 1600. The support arms 1605a-b may provide additional anchoring support to the sensor. Further, the support arm 1605a-b may latch into place as the sensor is slid into electrical engagement along the longitudinal axis of the sensor pin contacts (FIG. 3, item 320). When fully engaged, the sensor receptacle 1600 and the sensor may mate along a sensor receptacle latching surface and a sensor latching surface. In some examples, the latching operation may be releasable.

Although various embodiments have been described with reference to the figures, other embodiments are possible. For example, the MEMS element may be configured with various arrangements of apertures, and the apertures may be sized and spaced in a variety of ways. Various embodiments of aperture arrays may diffuse the incident gasses in various patterns upon the gel electrolyte. Examples of electrolyte gels are described in further detail with reference to, for example, US Patent Application Publication US 2004/0026246 (now U.S. Pat. No. 7,279,080), which is incorporated herein by reference in its entirety.

In some examples, a unique mechanical assembly for the gas sensor may solve issues associated with temperatures reaching 70° C. or higher. For example, a solid/gel electrolyte may be assembled with the gas sensor without the use of glues or adhesives. A mechanical assembly may provide a mechanical stack/snap feature that allows for a tight seal and a compression fit without the temperature of the gas sensor going above 70° C. Accordingly, the gas sensor may provide a small enough package to solve problems with high temperature (e.g., greater than 70° C.) assembly.

In some examples, electrical contacts integrated with the gas sensor assembly may electrically bring out signals from the gas sensor to other external electronic components. For example, the electrical connectors of the gas sensor may be configured to plug into a connector. Compression of the various parts of the gas sensor assembly may put various components into intimate contact which may advantageously minimize unwanted shaking of parts or loose electrical connections.

Various embodiments may use an electrolyte gel as an element of the design. The electrolyte may be a gel, which may greatly extend the life of the chemical sensor, in that the gel may not suffer from slow evaporation over time. By incorporating this gel into the design, the gas sensor may be a more durable, stable sensor, that may also have a small size footprint. Some embodiments may provide a gas sensor solution that can be surface mounted and survive a reflow oven.

The gas sensor, in some embodiments, may include an insert molded housing which carries four terminals. These terminals may be the working electrode (WE), the control electrode (CE), the diagnostic electrode (DE) and a reference electrode (RE). The design may create a central pocket with the control electrode, diagnostic electrode, and reference electrode all forming a plane in the bottom of the pocket and working electrode forming a contact plane higher up in the cavity. This may allow the gas sensor design to put a diffusion electrode into the bottom of the cavity allowing this element to make electrical contact to the various terminals. This diffusion electrode may have the electrolyte gel element stacked on top of it. On top of this electrolyte gel element, for example, may be placed another diffusion electrode that may actually be carrying the sample gas to be measured. The measurement may be made, for example, by allowing the chemical reaction to occur at the electrolyte-diffusion electrode-gas interface. This reaction may produce free electrons which flow electrically through the working electrode and are returned to the sensor at the control electrode. This principle of operation may make the reaction energy neutral.

In some embodiments, a MEMS silicon element is stacked into the design on top of the top diffusion electrode. The MEMS element may have holes pierced through it (e.g., using Deep Reactive Ion Etching) which allow the gas to feed the diffusion electrode to force the reaction. The face of the MEMS element may be coated with platinum and this platinum may be used for electrical conduction to the working electrode terminal. To hold this stack in compression, keep the silicon element in contact with the working electrode, and keep the diffusion electrodes in contact with the electrolyte, a compliant media seal (e.g., made of a synthetic/fluoropolymer elastomer/fluorosilicone rubber) may be placed between the MEMS element and the lid. The lid may be snapped onto the housing, compressing the media seal against the silicon element to force the stack into electrical contact. In order to keep the process stable with respect to environmental factors of temperature and pressure, the gas sensor may be run as a diffusion limited process. This may be controlled by limiting the diffusion of the sensed gas into the sensor with a restriction. The restriction may be created by making a small (e.g., 15 micron diameter) hole through the lid material for a distance of 1,500 microns, for example. This ratio of diameter to length (1:100) may create the restriction.

In some examples, the gas sensor may not be able to survive solder reflow. So a separate element may be used (an external electrical connector 1110), which can be SMT reflow mounted to a PCB. The four terminals on the gas sensor may be configured to couple with this external connector and allow the sensor to be mechanically slid into the connector on the PCB at room temperature without exposing the sensor to elevated temperatures.

Some embodiments of a compact gas sensor may provide a small, low cost sensor design that is achieved, for example, by a planar type of structure. A hybrid design of a gas sensor may include a solid (gel) polymer electrolyte combined with a MEMS element to effectively and efficiently diffuse gas laterally across the entirety of the top diffusion electrode layer. For example, by having many small capillaries in the MEMS element pressed up against the electrode, gas may efficiently spread out evenly and/or laterally through the top electrode structure, which may have the added benefit of minimizing the amount of free volume between the capillaries and the location where the gas chemical reaction is taking place. This may improve speed of response of the gas sensor and minimize effects due to pressure and temperature. Various examples may utilize a solid (gel) polymer electrolyte subassembly and a MEMS silicon element with capillaries to make efficient use of the electrode by restricting gas flow to spread gas evenly across an electrode.

In some examples, the capillaries of the MEMS element may distribute the gas to the diffusion electrode. Platinum and the incoming gas may be present in the diffusion electrode. Electrical current may be carried via the MEMS element between the (top) diffusion electrode and an electrical contact of the sensor housing. In various embodiments, the gas may spread out conically from each capillary into the diffusion electrode layer. The diffusion electrode may be about 50 microns thick. In some examples, the gas may pass through the diffusion electrode, which may be made at least partially of platinum, for example. In some examples, the smaller design of the gas sensor may change the amount of surface area interacting with the electrolyte. The sensor may allow for all the gas to be consumed when it is diffused down through the capillaries, which may advantageously provide for lower drift, and more repeatable operation of the gas sensor.

The ratio of the size of the capillary relative to the size of the electrode may optimize the amount of gas consumed through the capillaries. Optimization may be achieved by controlling the spacing between the capillaries relative to the thickness of the diffusion electrode. For example, the ratio of the spacing relative to the thickness may achieve an optimal result at setting the maximum of this ratio to 2:1 (e.g., the horizontal spacing of capillaries no more than twice the vertical height of the (top) diffusion electrode). This may be given by the equation $A/B<2$, where A is the distance between the capillaries and B is the height of the diffusion electrode. For example, optimization may advantageously produce a high signal to noise ratio. The electrical signal outputted by an electrical contact of the gas sensor may be proportional to the surface area of the (top) diffusion electrode.

In various embodiments, a gas sensor assembly (200) may include a sensor housing (205) having a cavity configured to receive an electrolyte subassembly (210). The gas sensor assembly may include a lid (225) configured to mechanically couple with the sensor housing, where the lid may include a gas inlet aperture (230) configured to permit fluid communication between ambient gasses around the gas sensor assembly and the cavity of the sensor housing. The gas sensor assembly may include the electrolyte subassembly (210, 900) disposed in the cavity of the sensor housing, where the electrolyte subassembly may include a top diffusion electrode layer (910), a bottom diffusion electrode layer (915), and, a gel electrolyte (905) sandwiched between the top diffusion electrode layer and the bottom diffusion electrode layer. The gas sensor assembly may include a micro electromechanical system (MEMS) element (215) lying between the sensor housing and the lid, where the MEMS element may include an array of capillaries configured to permit fluid communication between ambient gasses around the gas sensor assembly and the top diffusion electrode layer of the electrolyte subassembly via the gas inlet aperture. The gas sensor assembly may include a compliant media seal (220) lying between the sensor housing and the lid, such that the MEMS element is forcibly held in place by the compliant media seal and the lid.

The sensor housing may include at least one latch ledge (245). The lid may include at least one latching finger (235). In some examples, each of the at least one latching fingers may be configured to mechanically couple with a respective one of the at least one latch ledges of the sensor housing to mechanically couple the sensor housing with the lid. The sensor housing may include at least one latching ramp (240).

In various examples, each of the at least one latch ramps may be associated with a respective one of the at least one latch ledges, such that each of the at least one latching fingers translates along a respective one of the at least one latch ramps as the sensor housing is being assembled with the lid. In some embodiments, the at least one latching finger may be four latching fingers with each of the four latching fingers being disposed at a different corner of the lid. In some embodiments, the at least one latch ledge may be four latch ledges, with each of the four latch ledges being disposed at a different corner of the sensor housing. In some embodiments, the at least one latching ramp may be four latching ramps, with each of the four latching ramps being disposed at a different corner of the sensor housing.

In various embodiments, the gas sensor assembly may include electrical contacts (320) extending through the sensor housing and into the cavity of the sensor housing. The electrical contacts may include, for example, a working electrode (1015) electrically coupled to the top diffusion electrode layer via the MEMS element, a counter electrode (1020) electrically coupled to the bottom diffusion electrode layer, and a reference electrode (1030) electrically coupled to the bottom diffusion electrode layer. In various examples, the cavity of the sensor housing may include a stepped cavity having an upper deck (1005) and a lower deck (1010). In various examples, the working electrode may form a portion of the upper deck, and the counter and reference electrodes may form a portion of the lower deck. In some embodiments, the MEMS element may sit atop the upper deck, and the electrolyte subassembly may sit atop the lower deck.

Some embodiments may include a sensor receptacle (1110) comprising sensor pins (1205) each configured to electrically couple with a respective one of electrical contacts. The sensor receptacle may include at least one supporting latch arm configured to latchingly engage the sensor housing to support the sensor housing when the sensor housing is in electrical engagement with the sensor receptacle.

In some examples, a diameter of the gas inlet aperture may be approximately between 10-1000 μm, and a ratio of the diameter of the gas inlet aperture and a length of the gas inlet aperture through the lid may be 1:100. In some embodiments, the MEMS element may include silicon having a platinum-plated surface. In some examples, the inlet aperture of the lid may be configured to permit fluid communication between ambient gasses around the gas sensor assembly and the cavity of the sensor housing.

Various embodiments of the gas sensor may have the benefit of no water management issues, and therefore, the ability to miniaturize the sensor. Some examples are built as a two-electrode (e.g., working and counter electrodes) cell in a first instance, with the design enabling 3 or 4 electrode designs. Some embodiments may benefit from only using a very small electrode area. Some embodiments may use a two-electrode stacked design. In some examples, an electrode may only be active where it touches the electrolyte. In some embodiments, the spacing between capillaries may be comparable to electrode thickness to make optimum use of electrode area. Various embodiments may be environmentally friendly.

Some embodiments may utilize a hexagonal array of capillaries (e.g., capillary diameter: 15 μm; capillary length: 400 μm; array size: 5×6 mm; pitch: 100 μm; capillary density: 115.5/mm$^2$). Some embodiments may utilize a square array of capillaries (e.g., capillary diameter: 15 μm; capillary length: 400 μm; array size: 5×5 mm; pitch: 100 μm;

capillary density: 100/mm$^2$). A hexagonal array may advantageously give a more uniform utilization of electrode surface and allow higher sensitivity for a given electrode area or device size. A square array may be easier to design and manufacture.

In an exemplary embodiment, the dimensions of various components of a gas sensor may be as follows: electrode 50 µm thick; capillary spacing 100 µm; substrate 400 µm thick; capillary 15 µm diameter. These dimensions may vary by the above amounts, in some embodiments, by about 0.01, 0.1, 0.5, 1, 2, 3, 4, 5, 10, 20, 50, 100, 200, 500, or about 1000 µm or more. More capillaries may advantageously provide for a higher output current, which may be better for lower gas concentrations (e.g., environmental CO levels). In some embodiments, the total current may depend on total device size (e.g., 2×2 mm, 1.5×1.5 mm, or 1×1 mm. Some examples may include an electrolyte that is mechanically stable after a "reflow profile" of up to 150° C. Some exemplary dimensions of a gas sensor may be: 3 mm (length)×5 mm (width)×3.5 mm (height). The dimensions of the gas sensor may vary by the above amount, in some embodiments, by about 0.01, 0.1, 0.5, 1, 2, 3, 4, or about 5 or more millimeters.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A gas sensor assembly comprising:
    a sensor housing defining a cavity to receive an electrolyte subassembly;
    a lid configured to mechanically couple with the sensor housing, the lid defining a gas inlet aperture to permit fluid communication between ambient gases around the gas sensor assembly and the cavity of the sensor housing;
    the electrolyte subassembly disposed in the cavity, the electrolyte subassembly comprising:
    a top diffusion electrode layer,
    a bottom diffusion electrode layer, and
    a gel electrolyte sandwiched between the top diffusion electrode layer and the bottom diffusion electrode layer;
    a micro electromechanical system (MEMS) element lying between the sensor housing and a compliant media seal, the MEMS element comprising an array of capillaries configured to permit fluid communication between ambient gases around the gas sensor assembly and the cavity via the gas inlet aperture, wherein the MEMS element is in direct contact with the top diffusion electrode layer and a working electrode, the working electrode and the top diffusion electrode layer being different from each other; and
    wherein the lid is further configured to compress the compliant media seal against the MEMS element to force the electrolyte subassembly and MEMS element to stack into electrical conduction, wherein the MEMS element is forcibly held in place by the compliant media seal and the lid, wherein the gas inlet aperture defines a diffusion restriction based on a ratio between a diameter of the gas inlet aperture and a length of the gas inlet aperture.

2. The gas sensor assembly of claim 1, wherein:
    the sensor housing further comprises at least one latch ledge,
    the lid further comprises at least one latching finger, and
    each latching finger of the at least one latching finger is configured to mechanically couple with a respective latch ledge of the at least one latch ledge of the sensor housing to mechanically couple the sensor housing with the lid.

3. The gas sensor assembly of claim 2, wherein the sensor housing further comprises at least one latching ramp, wherein each latching ramp of the at least one latching ramp is associated with a respective latch ledge of the at least one latch ledge, such that each of the at least one latching finger translates along a respective latching ramp of the at least one latching ramp as the sensor housing is being assembled with the lid.

4. The gas sensor assembly of claim 3, wherein:
    the at least one latching finger comprises four latching fingers, each of the four latching fingers being disposed at a different corner of the lid,
    the at least one latch ledge comprises four latch ledges, each of the four latch ledges being disposed at a different corner of the sensor housing, and
    the at least one latching ramp comprises four latching ramps, each of the four latching ramps being disposed at a different corner of the sensor housing.

5. The gas sensor assembly of claim 1, further comprising electrical contacts extending through the sensor housing and into the cavity of the sensor housing, the electrical contacts comprising:
    the working electrode electrically coupled to the top diffusion electrode layer via the MEMS element,
    a counter electrode electrically coupled to the bottom diffusion electrode layer, and
    a reference electrode electrically coupled to the bottom diffusion electrode layer.

6. The gas sensor assembly of claim 5, wherein the cavity of the sensor housing comprises a stepped cavity having an upper deck and a lower deck, wherein:
    the working electrode forms a portion of the upper deck,
    the counter electrode and the reference electrode form a portion of the lower deck,
    the MEMS element sits atop the upper deck, and,
    the electrolyte subassembly sits atop the lower deck.

7. The gas sensor assembly of claim 5, further comprising a sensor receptacle comprising sensor pins each configured to electrically couple with a respective one of the electrical contacts.

8. The gas sensor assembly of claim 7, wherein the sensor receptacle further comprises at least one supporting latch arm configured to latchingly engage the sensor housing to support the sensor housing when the sensor housing is in electrical engagement with the sensor receptacle.

9. The gas sensor assembly of claim 1, wherein the ratio is 1:100.

10. The gas sensor assembly of claim 1, wherein the MEMS element comprises a platinum coating electronically connecting the sensor housing with the electrolyte subassembly.

11. A gas sensor assembly comprising:
    a sensor housing defining a cavity to receive an electrolyte subassembly;
    a lid configured to mechanically couple with the sensor housing, the lid defining a gas inlet aperture to permit fluid communication between ambient gases around the gas sensor assembly and the cavity of the sensor housing;

the electrolyte subassembly disposed in the cavity, the electrolyte subassembly comprising:
a top diffusion electrode layer, and
a bottom diffusion electrode layer; and
a micro electromechanical system (MEMS) element lying between the sensor housing and a compliant media seal, the MEMS element comprising an array of capillaries configured to permit fluid communication between ambient gases around the gas sensor assembly and the cavity via the gas inlet aperture, wherein the MEMS element is in direct contact with the top diffusion electrode layer and a working electrode, the working electrode and the top diffusion electrode layer being different from each other,
wherein the lid is further configured to compress the compliant media seal against the MEMS element to force the electrolyte subassembly and MEMS element to stack into electrical conduction, wherein the gas inlet aperture defines a diffusion restriction based on a ratio between a diameter of the gas inlet aperture and a length of the gas inlet aperture.

12. The gas sensor assembly of claim 11, wherein:
the sensor housing further comprises at least one latch ledge,
the lid further comprises at least one latching finger, and
each latching finger of the at least one latching finger is configured to mechanically couple with a respective latch ledge of the at least one latch ledge of the sensor housing to mechanically couple the sensor housing with the lid.

13. The gas sensor assembly of claim 12, wherein the sensor housing further comprises at least one latching ramp, wherein each latching ramp of the at least one latching ramp is associated with a respective latch ledge of the at least one latch ledge, such that each latching finger of the at least one latching finger translates along a respective latching ramp of the at least one latching ramp as the sensor housing is being assembled with the lid.

14. The gas sensor assembly of claim 13, wherein:
the at least one latching finger comprises four latching fingers, each of the four latching fingers being disposed at a different corner of the lid,
the at least one latch ledge comprises four latch ledges, each of the four latch ledges being disposed at a different corner of the sensor housing, and
the at least one latching ramp comprises four latching ramps, each of the four latching ramps being disposed at a different corner of the sensor housing.

15. The gas sensor assembly of claim 11, further comprising electrical contacts extending through the sensor housing and into the cavity of the sensor housing, the electrical contacts comprising:
the working electrode electrically coupled to the MEMS element,
a counter electrode electrically coupled to a first portion of the bottom diffusion electrode layer of the electrolyte subassembly, and
a reference electrode electrically coupled to a second portion of the bottom diffusion electrode layer of the electrolyte subassembly.

16. The gas sensor assembly of claim 15, wherein the cavity of the sensor housing comprises a stepped cavity having an upper deck and a lower deck, wherein:

the working electrode forms a portion of the upper deck,
the counter electrode and the reference electrode form a portion of the lower deck,
the MEMS element sits atop the upper deck, and,
the electrolyte subassembly sits atop the lower deck.

17. A gas sensor assembly comprising:
a sensor housing defining a cavity to receive an electrolyte subassembly;
a lid configured to mechanically couple with the sensor housing, the lid defining a gas inlet aperture for permitting fluid communication between ambient gases around the gas sensor assembly and the cavity of the sensor housing;
the electrolyte subassembly disposed in the cavity of the sensor housing, the electrolyte subassembly comprising:
a top diffusion electrode layer, and
a bottom diffusion electrode layer;
a micro electromechanical system (MEMS) element lying between the sensor housing and a compliant media seal, the MEMS element comprising an array of capillaries configured to permit fluid communication between ambient gases around the gas sensor assembly and the cavity via the gas inlet aperture, wherein the MEMS element is in direct contact with the top diffusion electrode layer and a working electrode, the working electrode and the top diffusion electrode layer being different from each other; and
the compliant media seal lying between the lid and the MEMS element, wherein the lid is further configured to compress the compliant media seal against the MEMS element to force the electrolyte subassembly and MEMS element to stack into electrical conduction, wherein the gas inlet aperture defines a diffusion restriction based on a ratio between a diameter of the gas inlet aperture and a length of the gas inlet aperture.

18. The gas sensor assembly of claim 17, wherein:
the sensor housing further comprises at least one latch ledge,
the lid further comprises at least one latching finger, and
each latching finger of the at least one latching finger is configured to mechanically couple with a respective latch ledge of the at least one latch ledge of the sensor housing to mechanically couple the sensor housing with the lid,
the sensor housing further comprises at least one latching ramp, wherein each latching ramp of the at least one latching ramp is associated with a respective latch ledge of the at least one latch ledge, such that each latching finger of the at least one latching finger translates along a respective latching ramp of the at least one latching ramp as the sensor housing is being assembled with the lid,
the at least one latching finger comprises four latching fingers, each of the four latching fingers being disposed at a different corner of the lid,
the at least one latch ledge comprises four latch ledges, each of the four latch ledges being disposed at a different corner of the sensor housing, and
the at least one latching ramp comprises four latching ramps, each of the four latching ramps being disposed at a different corner of the sensor housing.

19. The gas sensor assembly of claim 17, further comprising electrical contacts extending through the sensor housing and into the cavity of the sensor housing, wherein:

the electrical contacts comprise:
    the working electrode electrically coupled to the top diffusion electrode layer of the electrolyte subassembly via the MEMS element,
    a counter electrode electrically coupled to the bottom diffusion electrode layer of the electrolyte subassembly, and
    a reference electrode electrically coupled to the bottom diffusion electrode layer of the electrolyte subassembly,
the cavity of the sensor housing comprises a stepped cavity having an upper deck and a lower deck,
the working electrode forms a portion of the upper deck,
the counter electrode and the reference electrode form a portion of the lower deck,
the MEMS element sits atop the upper deck, and
the electrolyte subassembly sits atop the lower deck.

* * * * *